United States Patent
Fukui et al.

(10) Patent No.: US 9,303,257 B2
(45) Date of Patent: Apr. 5, 2016

(54) METHOD AND SYSTEM FOR CELL AND TISSUE CULTIVATION

(75) Inventors: Toshimi Fukui, Ohtsu (JP); Motoyuki Toki, Kyoto (JP)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 396 days.

(21) Appl. No.: 13/131,152

(22) PCT Filed: Jul. 1, 2010

(86) PCT No.: PCT/US2010/040725
§ 371 (c)(1),
(2), (4) Date: May 25, 2011

(87) PCT Pub. No.: WO2012/002967
PCT Pub. Date: Jan. 5, 2012

(65) Prior Publication Data
US 2012/0003709 A1    Jan. 5, 2012

(51) Int. Cl.
*C12M 1/00* (2006.01)
*C12M 3/00* (2006.01)
*C12N 13/00* (2006.01)
*C12M 1/12* (2006.01)
*C12M 1/26* (2006.01)
*C12N 11/00* (2006.01)

(52) U.S. Cl.
CPC ............... *C12N 13/00* (2013.01); *C12M 23/04* (2013.01); *C12M 23/20* (2013.01); *C12M 33/00* (2013.01); *C12N 11/00* (2013.01)

(58) Field of Classification Search
CPC ..... C12M 35/00; C12M 35/04; B01L 3/5027; B01L 2300/0819
See application file for complete search history.

(56) References Cited

U.S. PATENT DOCUMENTS

| | | | |
|---|---|---|---|
| 2,739,910 A | 3/1956 | McGarvey | |
| 3,197,325 A | 7/1965 | Hick et al. | |
| 5,153,136 A * | 10/1992 | Vandenburgh | 435/286.1 |
| 5,308,704 A | 5/1994 | Suzuki et al. | |

(Continued)

FOREIGN PATENT DOCUMENTS

| | | |
|---|---|---|
| JP | 2001-286162 | 10/2001 |
| JP | 2003-169847 | 6/2003 |

OTHER PUBLICATIONS

International Preliminary Report on Patentability & Written Opinion for PCT/US2010/040725 issued on Jan. 8, 2013.

(Continued)

*Primary Examiner* — Nathan Bowers
(74) *Attorney, Agent, or Firm* — Foley & Lardner LLP (57) ABSTRACT

A cell cultivating platform includes a substrate having a surface, at least one actuator moveable relative to the substrate, and a deformable material layer positioned above at least a portion of the supporting surface and the at least one actuator. The deformable material layer positioned opposite the substrate surface includes a biocompatible supportive surface suitable for supporting cultivated cells. The supportive surface deforms or otherwise deflects in response to activation of the at least one actuator, effectively releasing at least a portion of the cultured cells from the supportive surface. Suitable actuators include piezoelectric actuators that can be selectively energized according to one or more patterns to facilitate separation of cells from the supportive surface. Such activation cycles can be repeated.

20 Claims, 7 Drawing Sheets

(56) References Cited

U.S. PATENT DOCUMENTS

| | | | |
|---|---|---|---|
| 5,402,236 A * | 3/1995 | Brown et al. | 356/482 |
| 7,560,854 B2 | 7/2009 | Ohashi et al. | |
| 7,581,295 B2 | 9/2009 | Miyoshi | |
| 2004/0014205 A1 | 1/2004 | Banes | |
| 2004/0029266 A1 * | 2/2004 | Barbera-Guillem | 435/297.5 |
| 2005/0196321 A1 * | 9/2005 | Huang | 422/68.1 |
| 2006/0194309 A1 * | 8/2006 | Fuhr et al. | 435/289.1 |
| 2006/0270023 A1 | 11/2006 | LeDuc et al. | |
| 2008/0044893 A1 * | 2/2008 | Pollack et al. | 435/305.3 |
| 2008/0114144 A1 | 5/2008 | Shigemori et al. | |
| 2008/0238261 A1 | 10/2008 | Ohashi et al. | |
| 2009/0088342 A1 | 4/2009 | Moraes et al. | |
| 2010/0041128 A1 | 2/2010 | Banes et al. | |
| 2010/0159580 A1 | 6/2010 | Kim et al. | |
| 2010/0233799 A1 * | 9/2010 | Takayama et al. | 435/305.2 |
| 2010/0247384 A1 * | 9/2010 | Takayama et al. | 422/100 |
| 2010/0254837 A1 * | 10/2010 | Boersma et al. | 417/413.2 |

OTHER PUBLICATIONS

Furuyama, A. et al., "Assembly of basement membrane in vitro by cooperation between alveolar epithelial cells and pulmonary fibroblasts," Cell Struct. Funct., 1997, vol. 22, pp. 603-614.

International Search Report and Written Opinion for PCT/US2010/040725 mailed Sep. 7, 2010.

Pathak, S.S. et al., "Value addition to waterborne polyurethane resin by silicone modification for developing high performance coating on aluminum alloy," Progress in Organic Coatings, 2009, vol. 65, pp. 206-216.

Rao, S.V.S. et al., "Surface decontamination studies using polyvinyl acetate based strippable polymer," Journal of Radioanalytical and Nuclear Chemistry, 2004, vol. 260, No. 1, pp. 35-42.

Wikipedia webpage, "Thermal spraying," printed on Apr. 19, 2011, retrieved from the internet: <URL: http://en.wikipedia.org/wiki/Thermal_spraying>, 7 pages.

\* cited by examiner

METHOD AND SYSTEM FOR CELL AND TISSUE CULTIVATION

CROSS-REFERENCE TO RELATED APPLICATION

The present application is a U.S. national stage application claiming the benefit under 35 U.S.C. §371 of International Application No. PCT/US2010/040725, filed on Jul. 1, 2010, the entire contents of which is incorporated herein by reference in its entirety.

FIELD

The present technology relates generally to the field of tissue engineering, and more particularly to in vitro culturing of adherent cells.

BACKGROUND

There are two major types of cells grown in vitro: suspension cells (anchorage-independent cells) and adherent cells (anchorage-dependent cells). Suspension or anchorage-independent cells can multiply, in vitro, without being attached to a surface. In contrast, adherent cells generally attach to a surface in vitro during culture and proliferation, referred to herein generally as cell processing. Additionally, some typically non-adherent cells can proliferate on a surface that promotes adherent cell growth.

Cells are commonly cultured in a growth medium within containers (e.g., polystyrene) placed in enclosed incubators. In addition to providing a certain degree of isolation from pathogens, the incubators generally maintain a constant temperature, and a constant gas mixture.

Adherent cell culture systems require a surface on which to culture cells, such as a culture container or microcarrier (such as gelatin, porous glass, collagen or cellulose). The surface may also be coated with an extracellular matrix to increase adhesion properties. Feeder cells may also be used to coat the surface to provide a more adherent surface as well as providing nutrients to cultured cells. When the cells are ready to harvest, they must be removed from the culture surface. Adhesion of the cultured tissue to the surface generally makes removal a challenging task. An enzyme can be used to separate the cultured cells from the culture surface. Use of such enzymes or other chemicals or methods to separate cultured cells from the surface can cause damage to the tissue and even to the cultured cells, themselves.

SUMMARY

In some embodiments a cell cultivation platform includes a substrate having a surface, at least one actuator positioned relative to the substrate surface and configured to include at least two conformations, and a deformable material layer at least partially covering the substrate surface and the at least one actuator. The deformable material layer includes a biocompatible supportive surface configured to deform in response to a change in conformation of the at least one actuator.

In some embodiments, the at least one actuator is selected from the group consisting of: electromechanical actuators; hydraulic actuators; piezoelectric actuators; and combinations thereof. In particular, the at least one actuator can be a piezoelectric actuator selected from the group consisting of: Gallium orthophosphate ($GaPO_4$); Langasite ($La_3Ga_5SiO_{14}$); Barium titanate ($BaTiO_3$); Lead titanate ($PbTiO_3$); Lead zirconate titanate ($Pb[Zr_xTi_{1-x}]O_3$ $0<x<1$, known as PZT); Potassium niobate ($KNbO_3$); Lithium niobate ($LiNbO_3$); Lithium tantalate ($LiTaO_3$); Sodium tungstate ($Na_2WO_3$); $Ba_2NaNb_5O_5$; $Pb_2KNb_5O_{15}$; Sodium potassium niobate (Na-KNb); Bismuth ferrite ($BiFeO_3$); $NaNbO_3$; Polyvinylidene fluoride (PVDF); and combinations thereof.

In some embodiments, the at least one actuator can have a diameter between about 100 nm and about 5 mm. When the actuators are separated by an interval therebetween the interval may be about 10 µm to 5 mm, about 15 µm to 4 mm, about 20 µm to 3 mm, about 30 µm to 2 mm, about 40 µm to 1 mm, and about 50 µm to 1 mm and so forth.

The actuators can be arranged on the supporting surface as an array. The array can include at least one row, and in some instances form a lattice or grid.

The substrate can be selected from the group consisting of: glass; ceramic; polyvinylchloride; polystyrene; polyurethane; and combinations thereof. In some embodiments, the substrate is contoured according to a portion of a cell processing chamber.

The deformable material layer can be selected from the group consisting of: polyurethane; polystyrene; polyvinylchloride; and combinations thereof. The deformable material layer can be formed as a coating covering at least a portion of the supporting surface and the at least one actuator. Thickness of the deformable material layer above the supporting surface is sufficient to cover the at least one actuator, while allowing substantial deformation of the supportive surface in response to activation of the at least one actuator.

In some embodiments, the substrate includes an interdigitation portion around at least a portion of an edge configured for interlocking engagement with a corresponding interdigitation portion of a container wall. The wall is also fitted with the interdigitation part and configured for interlocking engagement.

In some embodiments when configured for activation by electrical energy, at least one electrical lead is also provided in electrical communication with the at least one actuator. The energy source, when provided, is in electrical communication with the at least one actuator through at least one switch coupled to the at least one electric lead and positioned between the at least one actuator and the energy source. In some embodiments, a controller is supplied in communication with the at least one switch. The controller is configured to operate the at least one switch according to a peel protocol.

In some embodiments, a process facilitates the harvest of cultivated cells. Energy is supplied to activate the at least one actuator positioned between a substrate surface and a supportive surface of a cell culture chamber configured to support one or more cells thereon. At least a portion of the supportive surface is deformed in responsive to activation of the at least one actuator. Such deformation is configured to at least partially displace one or more cells supported thereon relative to the supportive surface.

In some embodiments, the act of supplying energy comprises selectively supplying voltage to at least one actuator, wherein the at least one actuator is a piezoelectric actuator. The voltage can be selected from a range of voltages, for example, between about 0.5 V to 100 V, about 1 V to 80 V, about 3 V to 50 V, about 5 V to 30 V, about 5 V to 20 V, and about 5 V to 10 V.

In some embodiments, selectively supplying voltage comprises supplying voltage to all of the at least one actuators. Selectively supplying voltage can include supplying a first voltage to all of the at least one actuators during a first time interval, supplying a second voltage to all of the at least one actuators during a second time interval and repeating supply of the first and second voltages to all of the at least one actuators in alternating succession.

In some embodiments selectively supplying voltage comprises supplying voltage to a first subset of the at least one actuators, the first subset being less than all of the at least one actuators. Selectively supplying voltage can include supplying a first voltage to a first subset of the at least one actuators during a first time interval, supplying a second voltage to a second subset of the at least one actuators during a second time interval and repeating supply of the first and second voltages, respectively, to the first and second subsets of the at least one actuator in alternating succession.

In some embodiments, a cell culture chamber includes along at least a portion of one surface a cell cultivating platform according to any of the embodiments described above.

In yet other embodiments a cell cultivating platform includes means for supporting cultured cells along at least a portion of a surface relative to a cell culture chamber. The platform also includes means for supplying energy to activate the at least one actuator positioned between a substrate and the supportive surface and means for deforming at least a portion of the supportive surface responsive to activation of the at least one actuator. Such deformation displaces one or more cells of a cultured tissue sample relative to the supportive surface.

BRIEF DESCRIPTION OF THE DRAWINGS

The foregoing and other objects, features and advantages of the technology will be apparent from the following more particular description of embodiments of the technology, as illustrated in the accompanying drawings in which like reference characters refer to the same parts throughout the different views. The drawings are not necessarily to scale, emphasis instead being placed upon illustrating the principles of the technology.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The present technology provides a process and device for use in the culture or proliferation of cells. Some embodiments of such a device include a substrate including one or more electrical wires, one or more piezoelectric actuators positioned relative to the substrate, and a coating material at least partially covering one or more of the substrate and the actuator, as may be advantageous for electrical insulation. Such a device applies piezoelectric elements as actuators to separate cultured cells in a culture container. As a result, the cultured cells may be separated from the substrate without the use of chemicals, or with a reduced amount of chemicals and/or a reduced chemical application time as compared to existing systems. The piezoelectric actuators expand/contract three-dimensionally and uses a piston motion to lift up and down the cultured cells so that the cultured cells/tissues can easily be peeled off from the container.

Figure 1A:
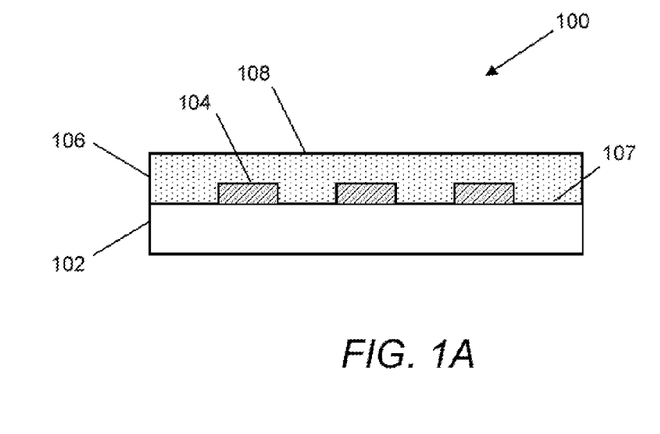
FIG. 1A illustrates a side view of an illustrative embodiment of a self-releasing, tissue cultivating surface in a deactivated state.
Figure 1B:
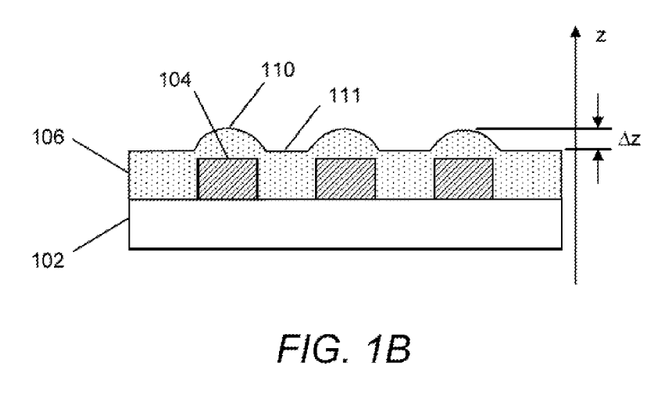
FIG. 1B illustrates a side view of an illustrative embodiment of the self-releasing, tissue cultivating surface of FIG. 1A in an activated state.

An illustrative embodiment of a self-releasing, tissue cultivating platform 100 is illustrated in FIG. 1. As used herein, the term "self-releasing" refers to capabilities related to peeling or otherwise separating, at least partially, one or more cells or cellular tissue from a surface of the platform 100 without physical intervention beyond the system itself. Self-releasing can also refer to the separating of one or more cells or cellular tissue from the surface without the use of any chemicals such as trypsin. Self-releasing can further refer to the separating of one or more cells or cellular tissue from the surface with the use of a reduced amount of chemicals as compared to traditional systems and/or with the use of chemicals for a shorter period of time as compared to traditional systems. The platform 100 includes a substrate 102, a plurality of actuators 104 positioned on the substrate 102 and a supportive layer 106. As described in more detail below, the supportive layer 106 is responsive to activation of one or more of the plurality of actuators 104. The supportive layer 106 includes a deformable supportive surface 108 upon which cells can be cultivated. The surface 108 is made from a biocompatible material, such that adherent cells can be cultivated thereon. Generally, the biocompatible materials can include materials known to those of skill in the art for use in a cell culture environment. Examples of such materials include polymers, polyvinyl acetate (PVA), polyurethane, polystyrene, polyvinylchloride, rubbers, synthetic rubbers, and the like.

In the illustrative embodiment, the substrate 102 includes a supportive surface 107, at least a portion of which is in contact with the plurality of actuators 104. The flexible, supportive layer 106 is positioned along the same surface 107, covering the plurality of actuators 104, such that none of the actuators 104 are exposed to the deformable, supportive surface 108 or to the cell culture media. In at least some embodiments, a shape of the deformable, supportive surface 108 substantially follows a contour of the underlying substrate surface 107 and the actuators 104. The shape of the deformable, supportive surface 108 can be flat as shown, or contoured, as in a curve or angle according to a shape of a cell cultivating chamber (not shown). For example, the surface 108 can be curved to accommodate the shape of a side wall of a dish, beaker, or other cell cultivating chamber.

When the actuators 104 are actuated, the deformable, supportive surface 108 is reshaped to induce at least partial displacement of cells of any tissue layer positioned thereon, such as a cultivated tissue layer, referred to herein as peeling. Such peeling action can be sufficient to induce at least a partial separation of an adherent cell culture from the surface 108. For example, such peeling may substantially separate one or more cells, or cellular tissue from the surface 108, thereby facilitating removal of the one or more cells, or cellular tissue from the cell processing chamber. Alternatively or in addition, such peeling may partially separate or otherwise loosen some of the one or more cells or a portion of the cellular tissue, thereby facilitating physical removal (e.g., at least partially physically peeling with or without further assistance from the actuators) from the cell processing chamber. The size of the tissue-cultivating platform 100 may depend on the surface area of a culture container to be used. In at least some embodiments, more than one platform 100 can be arranged (e.g., side-by-side) to cultivate a single layer of tissue.

Substrate/Actuator.

The actuators 104 are generally arranged to cause a deformation of the deformable, supportive surface 108 to induce cell separation and/or cell peeling. In some embodiments, the actuators 104 are linear actuators, extending or otherwise expanding in response to an activating stimulus. In some embodiments, such extension or expansion among multiple actuators 104 occurs along a substantially common direction. Such actuators 104 can include electromechanical actuators, hydraulic actuators (e.g., microfluidic devices) or piezoelectric actuators.

In the illustrative embodiment, piezoelectric actuators 104 are positioned along the surface 107 of a substantially hard, or rigid substrate 102. The substrate can be substantially rigid, such that deflection of actuators 104 extends away from the surface 107. That is, the substantially rigid substrate forms a surface or platform substantially preventing deflection of the actuators 104 in a direction toward the substrate surface 107. Upon activation, the piezoelectric actuators 104 expand. Such expansion can occur in a direction normal to the surface 107, parallel to the surface 107, or at any angle between 0 and 180 degrees relative to the surface 107. In at least some embodiments, the actuators 104 are suitably aligned to expand in a direction substantially normal to the surface 107 (they may also expand in other dimensions to a greater or lesser extent). The rigid surface 107 promotes expansion of such suitably aligned actuators 104 to occur in a direction normal to the surface 107 (e.g., away from the surface).

As illustrated in FIG. 1B, each expanded or extended actuator 104 causes a respective, localized deformation of the flexible supportive layer 106. Preferably, the supportive layer 106 is relatively thin and flexible, or elastic, such that deformation of the actuator 104 induces a corresponding, localized deformation of the supportive surface 108. In at least some embodiments, the supportive layer is resilient, returning to its quiescent state (e.g., following a surface contour of the cell processing chamber, such as along a cylindrical wall, or along a flat wall or bottom) upon deactivation of the actuators 104. In the illustrative embodiment, all actuators 104 are activated substantially simultaneously, expanding in a direction normal to the surface 107. In the illustrative example, the surface 107 is positioned in the x-y plane. The rigid substrate 102 ensures that the expansion of the actuators 104 occurs in a direction normal to and away from the surface 107 (i.e., in the positive z-direction). Each of the actuators 104 is spaced apart from neighboring actuators 104, such that the deformable surface 108 bends to form raised areas 100, or peaks with respect to adjacent areas, or troughs 111.

It is contemplated that in some embodiments, the actuators 104 are normally in an expanded state, such that the deformable, supportive surface is relatively smooth or flat for cell cultivation. During a peeling protocol, the actuators 104 are contracted (e.g., deactivated), again deflecting in a direction normal to, but towards the surface 107 (i.e., in the negative z-direction). Each of the actuators 104 is similarly spaced apart from neighboring actuators 104, such that the deformable surface 108 bends to form depressed areas (not shown), such as dimples or valleys, with respect to adjacent surface areas.

In some embodiments, at least some of the plurality of actuators 104 are normally extended and at least some other of the plurality of actuators 104 are normally contracted, the deformable supportive surface 108 being substantially flat in a quiescent, or cell-culturing state. During a peeling protocol, the normally extended actuators 104 are contracted and the normally contracted actuators 104 are extended. In certain arrangements, adjacent ones of such actuators 104 can result in a greater relative deflection of the deformable, supportive surface 108 than either actuator would be capable of producing alone (i.e., a surface deflection approaching $2\Delta z$ for individual actuator deflections of $\pm \Delta z$).

Such expansions or contractions of the actuators 104 can be referred to generally as conformations. Conformations of the actuators 104 can include, in a non-limiting sense: extensions in one or more of length, width or height; contractions in one or more of length, width or height; formation of a bend; removal of a bend; formation of a convex shape; formation of a concave shape, and the like. One or more of the actuators 104 can be configured to conform in a similar sense, in a different sense, or in a combination of similar and different senses. For example, some actuators 104 can be configured to extend, while others are configured to contract along the same supportive surface.

The substrate 102 at the bottom of the device can be formed of any suitable supportive material. Various material generally used for substrates may be used such as but not limited to glass, ceramic, polyvinylchloride, polystyrene, polyurethane, and the like. The substrate 102 can be electrically connected to the piezoelectric actuators 104. For example, an electrical circuit can be formed on or in the substrate, selectively coupling each of the plurality of actuators 104 to an energy source. An illustrative circuit is described in more detail below.

The actuators 104 themselves can include one or more of various piezoelectric materials. Examples of such materials include orthophosphate ($GaPO_4$), Langasite ($La_3Ga_5SiO_{14}$), Barium titanate ($BaTiO_3$), Lead titanate ($PbTiO_3$), Lead zirconate titanate ($Pb[Zr_xTi_{1-x}]O_3$ $0<x<1$, known as PZT), Potassium niobate ($KNbO_3$), Lithium niobate ($LiNbO_3$), Lithium tantalate ($LiTaO_3$), Sodium tungstate ($Na_2WO_3$), $Ba_2NaNb_5O_5$, $Pb_2KNb_5O_{15}$, Sodium potassium niobate (Na-KNb), Bismuth ferrite ($BiFeO_3$), $NaNbO_3$, and Polyvinylidene fluoride (PVDF).

When an appropriate voltage is applied to a piezoelectric actuator, the actuator changes size, expanding and/or contracting itself. Embodiments of this disclosure use this property of actuators to weaken any association between cultured cells and the supportive surface in a process referred to herein as "a peel" or "peeling." The shape of the actuator may vary, including shapes such as but not limited to, cylindrical, cubical, linear (straight, curved, combinations of either), and so on. The illustrative embodiments include actuators extending in at least two dimensions along the supportive surface. Actuator can be shaped as regular shapes, such as rectangles, or circles. The diameter (or a side) of such actuators may be about 100 μm to about 5 cm, about 150 μm to about 4 cm, about 200 μm to about 3 cm, about 300 μm to about 2 cm, about 400 μm to 1 cm, 500 μm to about 1 cm, and so forth. Cell sizes vary depending upon the particular cell culture, such that the relative size and deflection range of any piezoelectric actuators can be selected in response thereto. In an illustrative embodiment, a range of actuator deflection can be between approximately 1 μm and approximately 1 millimeter (mm) relative to the substrate. In alternative embodiments, other values for actuator deflection (such as less than 1 μm or greater than 1 mm) may be used. The piezoelectric actuators can be shaped and sized to induce a peel, without substantially damaging or otherwise tearing cultured cells or tissues formed from the cultured cells.

In an illustrative example, a 6 cm diameter circular substrate, such as may be used with a 6 cm diameter culture dish, includes one or more disk-shaped actuators distributed across a substrate surface facing the interior of the chamber and having a diameter of about 1 mm. In some embodiments, a single actuator can be provided to lift at least a portion of an adherent cell structure of the supportive surface, such that another tool can be used to grasp a portion of the cell structure. In such a manner, a peel is initiated by the actuator, but completed by the separate tool (e.g., tweezers, forceps, fingers). In the 6 cm diameter culture dish example having a single actuator, the actuator may be relatively small (e.g., 5 mm) raising a small portion of the cell structure, or relatively large (e.g., 5 cm) raising a large portion of the cell structure.

The range of the applied voltage and the cycle (apply on/off) depends on various conditions like type of cultured cells, the culturing surface area, and so on. For instance, the range of the voltage to change the shape of the actuator can be about 10V to 100V, about 20V to 100V, about 30V to 100V, about 40V to 100V, and about 50V to 100V.

To separate the cultured cells efficiently with each culture purpose, the plurality of actuators 104 can be arranged on the surface 107 of the substrate 102 in various alignments such as but not limited to arrays, lattices, rows, and the like, also including irregular, or randomized patterns, and combinations of one or more such alignments. For example, a first alignment can be used along an interior region; whereas, a different alignment can be used along a perimeter region. Generally, piezoelectric actuators 104 expand both horizontally and longitudinally, such that some interval or separation is provided between actuators. The intervals may be about 10 μm to 5 mm, about 15 μm to 4 mm, about 20 μm to 3 mm, about 30 μm to 2 mm, about 40 μm to 1 mm, and about 50 μm to 1 mm and so forth. The spacing of the intervals can be regular, irregular, or combinations or regular and irregular.

During the deactivated state, a resting diameter of the actuator measured parallel to the surface 108 can be about 100 nm to about 5 mm. In embodiments where the actuator is able to contract/expand, the diameter in an activated state can be about 105 nm to about 5.5 mm. A resting height of the actuator measured normal to the surface 108 can be about 300 nm to about 4.5 mm. In embodiments where the actuator is able to contract/expand, an actuated length of the actuator can be about 310 nm to about 6 mm.

As described above, the flexible, supportive layer 106 forms a coating or covering over at least a portion of the substrate 102 and actuators 104. Electricity is applied to piezoelectric actuators 104, for example via the substrate and in at least some embodiments, the actuators are ferroelectric elements. Preferably, the supportive layer 106 also provides an environmental seal, separating the actuators 104 and related circuitry from cultured cells and culture medium.

Various materials can be used for the flexible, supportive layer, providing that they are electrically insulating and moisture proof. In at least some embodiments, such materials are also biocompatible and relatively inert so as not to interfere with cell culture or the cell culture environment. Suitable materials can be resilient, naturally returning to a rest state (e.g., smooth), after actuation (e.g., rippled or dimpled). Examples of suitable coating materials include polymers, polyvinyl acetate (PVA), polyurethane, polystyrene, polyvinylchloride, rubbers, synthetic rubbers, and the like. The thickness of the coating may be about 1 μm to 50 μm, about 1 μm to 30 μm, about 1 μm to 10 μm, and so forth. There are various methods for coating those coating material polymer and the following references can be referred for PVA coating: U.S. Pat. Nos. 3,197,325 and 2,739,910, and "S. V. S. Rao, and K. B. Lal, Journal of Radioanalytical and Nuclear Chemistry, Vol. 260, No. 1 (2004) 35-42" (http://www.springerlink.com/content/t926x4948805v1w0/fulltext.pdf?page=1) and so on, incorporated herein by reference in their entireties. For polyurethane, the following references can be referred: "Progress in Organic Coatings Volume 65, Issue 2, June 2009, Pages 206-216" (http://www.sciencedirect.com/science?_ob=ArticleURL&_udi=B6THD-4VC73YB-1&_user=10&_rdoc=1&_fmt=&_orig=search&_sort=d&_docanchor=&view=c&_acct=C000050221&_version=1&_urlVersion=0&_userid=10&md5=7aad2b566ab4b7221900b0109ed82dd1), U.S. Pub. Pat. App. 2008/114,144(A1), also incorporated herein by reference in their entireties, and the like.

In some embodiments, the flexible, supportive layer 106 includes more than one layer. For example, one or more topcoats can be applied to improve performance, such as sealability, biocompatibility, etc. To improve adhesion property (for cells) of the coating material, ion implantation technique can be used (Ref: U.S. Pat. No. 5,308,704, incorporated herein by reference in its entirety) to modify the surface of the coating material to improve the adhesion property for cell culture.

The device may further provide a sealing packing material on the coating material to make the insulation much tighter. For the sealing, known materials such as silicon can be used and the material can be set along the corner between the wall area and the edge of the substrate (e.g., a gasket, or O-ring).

This device/actuators can be made using semiconductor technology, such as photolithography and the like. (Ref: U.S. Pub. Pat. App. 2008/0238261 A1, U.S. Pat. Nos. 7,560,854 B2, 7,581,295 B2, etc., all incorporated herein by reference in their entireties). The coating material may be formed with known art such as spray method and the like (http://en.wikipedia.org/wiki/Thermal_spraying).

Figure 2A:
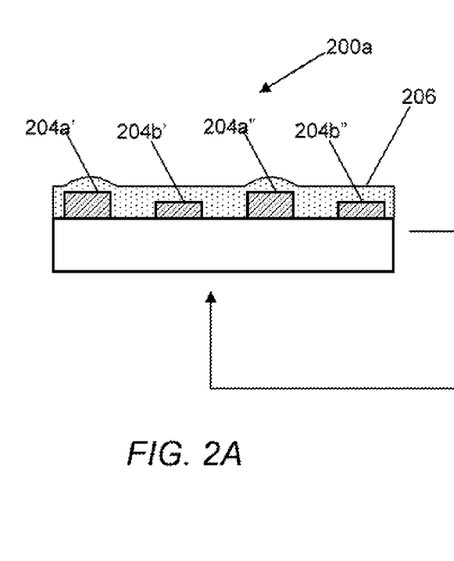
FIG. 2A illustrates a side view of another illustrative embodiment of a self-releasing, tissue cultivating surface in an activated state.
Figure 2B:
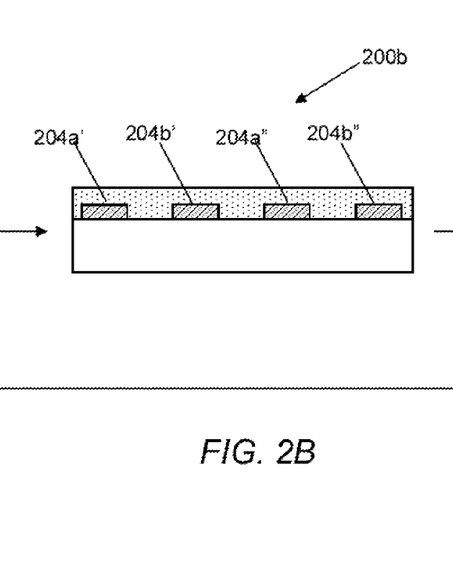
FIG. 2B illustrates a side view of an illustrative embodiment of the self-releasing, tissue cultivating surface of FIG. 2A in a deactivated state.
Figure 2C:
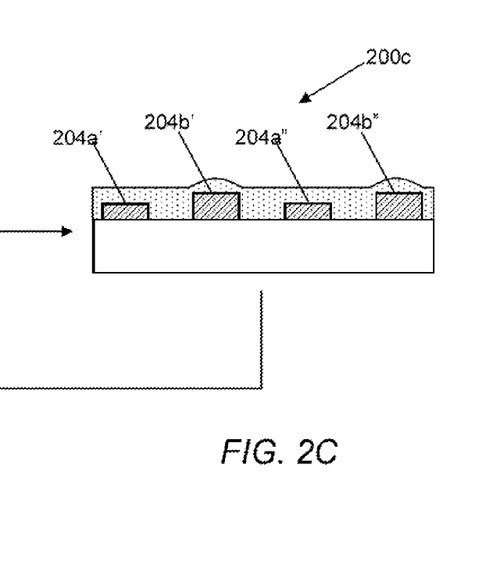
FIG. 2C illustrates a side view an illustrative embodiment of the self-releasing, tissue cultivating surface of FIG. 2A and FIG. 2B in another activated state.

In some embodiments, substantially all of the piezo-actuators can be activated together during a peeling protocol as illustrated in FIG. 1B. Such peeling protocols can include alternating between such activated and deactivated states (i.e., FIG. 1B and FIG. 1A) according to a cycle. At least with respect to piezo-actuators, activation refers to an extended or expanded state as may be obtained in response to the application of a driving voltage; whereas, deactivation refers to a non-extended or contracted state as may result from the absence of any such driving voltage. Such cycles can include a predetermined sequence of one or more activations and deactivations, such as on-off-on-off, etc.). In other embodiments, only a subset of the piezo-actuators is activated at any one time. Referring to FIG. 2A, an illustrative embodiment of a self-releasing, tissue cultivating platform 200a in a first active state, including a first activated (i.e., expanded) subset of actuators 204a', 204a" (generally 204a), and a second deactivated (i.e., contracted) subset of actuators 204b', 204b" (generally 204b). The first and second subsets of actuators 204a, 204b can be arranged in an alternating pattern, as shown. FIG. 2B illustrates the platform 200b in a deactivated state in which substantially all of the actuators 204a, 204b are deactivated. FIG. 2C, illustrates the platform 200c in a second active state in which the first subset of actuators 204a is deactivated, and the second subset of actuators 204b is activated.

Arrows drawn between FIG. 2A, FIG. 2B and FIG. 2C, suggest that the different activation patters can be applied in succession, for example, during a peeling protocol. As illustrated, the first active state provides an activation pattern expanding only the first subset of actuators 204a (FIG. 2A). An intermediate state allows all actuators to return to a deactivated state (FIG. 2B), followed by a second active state, providing a second activation pattern expanding only the second subset of actuators 204b (FIG. 2C). The peeling protocol or process can be repeated according to the sequence shown (e.g., FIG. 2A, FIG. 2B, FIG. 2C, FIG. 2A, and so forth), or according to variations of such a sequence (e.g., FIG. 2A, FIG. 2B, FIG. 2C, FIG. 2B, FIG. 2A, and so forth). In some embodiments, the intermediate state (FIG. 2B) is not implemented, such that the peeling protocol repeats successively between the patterns of FIG. 2A and FIG. 2C.

Figure 3A:
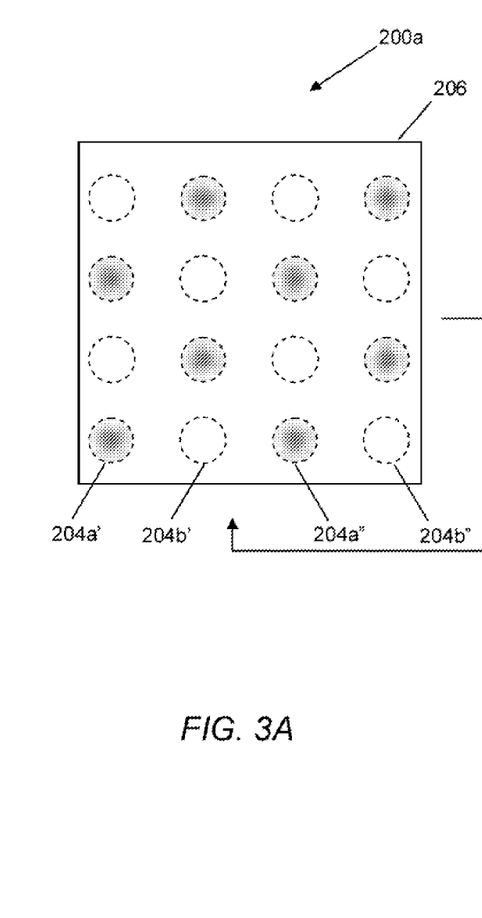
FIG. 3A illustrates a top view of an illustrative embodiment of the self-releasing, tissue cultivating surface of FIG. 2A.
Figure 3B:
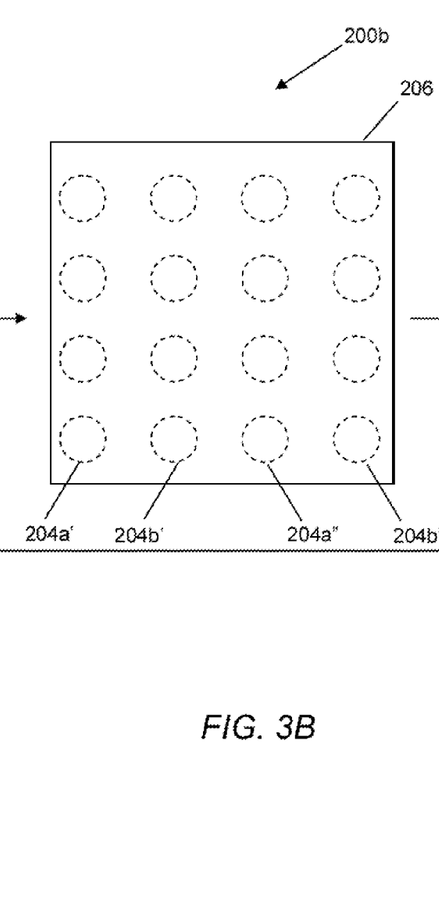
FIG. 3B illustrates a top view of an illustrative embodiment of the self-releasing, tissue cultivating surface of FIG. 2B.
Figure 3C:
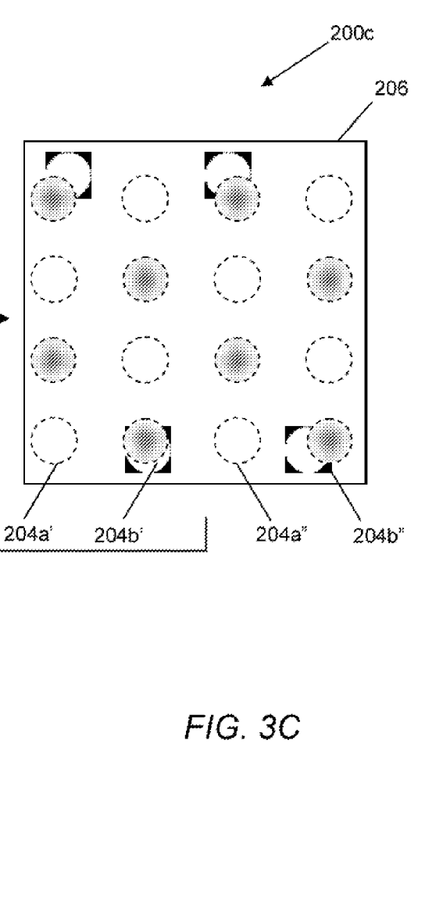
FIG. 3C illustrates a top view of an illustrative embodiment of the self-releasing, tissue cultivating surface of FIG. 2C.

Referring next to FIG. 3A through 3C, a top view of the illustrative self-releasing, tissue cultivating platform 200 is shown. The individual actuators 204a, 204b are arranged in a grid beneath the flexible, supportive layer 206, shown in phantom. As partially activated, the actuators can be moved alternately as described above in reference to FIG. 2A through FIG. 2C, and in an alternating fashion row-by-row, forming a checkerboard pattern of the first and second actuators 204a, 204b. Preferably, such activation of the actuators can peel off the cultured cells without damage. Since piezoactuator's motion is easily controlled by electrical condition, this configuration provides suitable motion (motion pattern) depending on the type of cells to be cultured, or other conditions, to harvest the cultured cells efficiently. Other patterns of on-off actuators can be implemented, such as lines, curves, larger checkerboard patterns, where groups of adjacent actuators are energized together as a single larger actuator, etc.

Figure 4:
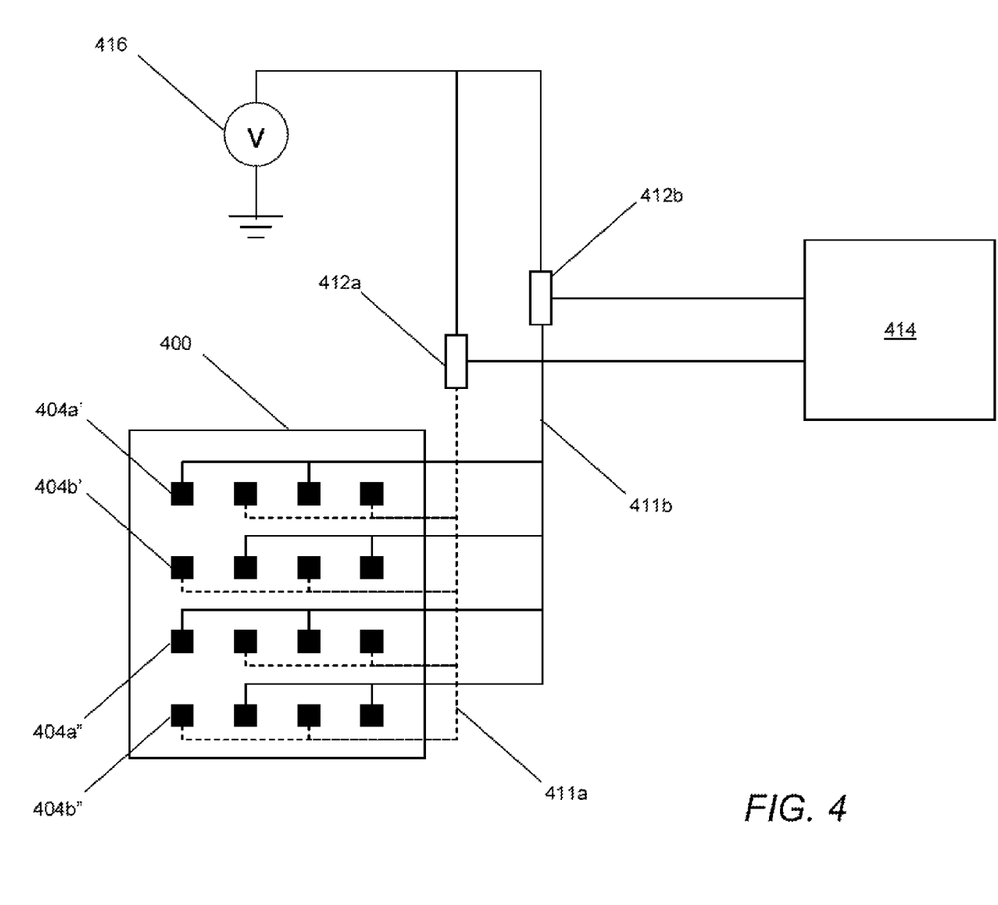
FIG. 4 illustrates a schematic diagram of an illustrative embodiment of a self-releasing, tissue cultivating device.

A schematic diagram of one embodiment of a self-releasing, tissue cultivating device is shown in FIG. 4. A plurality of piezo-actuators 404a, 404b are arranged in a grid pattern. A first subset of piezo-actuators 404a', 404a" (generally 404a) are interspersed with a second subset of piezo-actuators 404b', 404b" (generally 404b) to form a checkerboard pattern. The first subset of piezo-actuators is electrically coupled to an energy source 416 through a first circuit path, or lead 411a. Similarly, the second subset of piezo-actuators is electrically coupled to the energy source 416 through a second circuit path, or lead 411b. First and second switches 412a, 412b are respectively provided between the energy source 416 and the first and second subsets of actuators 404a, 404b to selectively control application of energy thereto. In some embodiments, each of the actuators can be independently and individually controlled.

In some embodiments, a controller 414 controls operation of the switches 412a, 412b (generally 412). The switches 412 can be any suitable switch, including mechanical switches, electro-mechanical switches, electrical switches, such as transistor switches. The controller 414 can be a customized controller executing a switch protocol, or a general purpose computer implementing pre-programmed instructions to implement a switch protocol. In either instance, control can be initiated by a user, or according to a scheduled cycle of cell culture growth and peel. In some embodiments, a growth-peel cycle can be repeated for the same tissue, periodically separating or peeling tissue from the tissue-cultivating device at one or more instances during cultivation of the tissue.

Configuration of the Device and a Cell Culture Container.

In one embodiment, the self-releasing, tissue cultivating platform is shaped to fit in a suitable container used for cell culture. Such containers include bio reactors, beakers, bags, dishes, molds, and the like. In at least some embodiments, the self-releasing, tissue cultivating platform can be placed into such a container to cultivate cells thereon. In such cases, any wiring between the self-releasing, tissue cultivating platform and energy source, electric generator, or control would be covered, for example by an insulating polymer set along the inside of the container wall. Examples of such insulating polymers include polyvinyl acetate (PVA), polyurethane, polystyrene and the like.

Alternatively or in addition, the self-releasing, tissue cultivating platform is placed along a bottom of a cell culture container and along a wall part of the container. In some embodiments, the self-releasing, tissue cultivating platform includes separate sections. For example, in a cylindrical, or dish-shaped processing chamber, the self-releasing, tissue cultivating platform includes a circular or disc-shaped bottom section and a cylindrical or otherwise ring shaped side section or side wall. Each section can be used alone or in combination. When used in combination, the bottom section can be assembled with the wall section forming an open cylindrical self-releasing, tissue cultivating platform. In such combination embodiments, one or more of the sections may have an interdigitation part, for example, around an edge, to interlock with a mating section. Continuing with the dish-shaped example, the circular bottom section can include one or more peripheral projections or recesses sized, positioned, and otherwise configured to interlock with one or more complementary recesses or projections located along an adjacent end of the side wall section. In some embodiments the circular bottom section may be interlocked with the side wall section without the interdigitation part, instead using a joining or sealing material, such as silicon packing positioned around the intersection of the circular bottom section and the side wall section.

More generally, shapes of the various self-releasing, tissue cultivating sections useable in a cell processing container can follow contours of adjacent container sections, like the bottom of a container, a wall part of a container, a shaped substrate to cultivate cellular structures having predetermined shapes, and the like. Shapes and sizes of various sections can be provided to accommodate standard cell processing chambers. These may include circular base sections of various diameters, cylindrical wall sections of various diameters and heights, as well as sections of other shapes and sizes, all usable alone or in combination to provide a suitable tissue-cultivating surface in a cell processing chamber.

When such sections are provided with interdigitation parts to fit with adjacent sections (e.g., when the interdigitation structure is provided for both parts). The various sections can engage each other. Such interconnections can include electrical interconnections between sections to facilitate wiring and handling of such devices. For example, a single external electrical connection can be made to a wall section of a multi-section configuration. The wall section can be electrically interconnected to a base section, such that control of actuators on the wall and base sections can be accomplished by the single external electrical connection—no additional external wiring is necessary to control the base section. In some embodiments, any of the devices described herein can be configures as a disposable cassette device.

The processes and devices described herein can be beneficial to the processing of various types of cells. Illustrative types of cells that can be cultured and isolated include any type of cells or tissues that at least partially adhere to culture containers, referred to herein as adherent or adhesive cells. Adhesion suggests that the cells or tissues display a tendency to stick to or otherwise maintain intimate contact with a container surface, thereby making it difficult to remove such cells or tissues. Such adhesive cells may include, but are not limited to, stem cells, follicle cells, epidermal cells, osteoblasts, and the like. Such cells are typically cultured in a fluid environment referred to as a cell culture medium. Conventional cell culture mediums, such as saline, bovine serum, nutrients, and the like, can also be used since the actuators are stable in most mediums.

Culture Method.

The self-releasing, tissue cultivating platform or surface facilitates cell or tissue harvesting, by preventing damage (e.g., tearing) during separation of the cells or tissue. Namely, the actuators are operated to effectively peel cultured cells off of the cell-culture surface. In various embodiments, the actuators can be operated to act independently of each other as described herein. Mechanical movement or deformation of the surface breaks adhesiveness that may have formed between target cells and cells adjacent to the target cells.

In some embodiments, a lifting action breaks physical bonds existing between adjacent target cells, or at least loosens the bonds existing therebetween. In some embodiments, repeated actuation of the actuators may be necessary so that the actuator goes through multiple cycles of activation/deactivation (much like a piston action). In one embodiment, the number of cycles to loosen the bonds between target cells and adjacent target cells is about 1 cycle to about 10 cycles over a period of about 30 seconds. The number of cycles may depend on a number of factors such as the size of the actuator, the type of target cell that is located on the actuator, and the density of the actuators. For example, larger actuators may provide more lift force so that fewer cycles are required versus smaller actuators that may provide less lift force.

In another example, certain types of target cells may experience greater adhesion with the actuator than other types of target cells due to difference in extracellular matrix, functional groups, proteins or other binding sites that may exist on the wall of the target cell. In yet another example, target cells that are closer together may require more lifting cycles to loosen the bonds between them versus target cells that are further apart and may not experience as great of bonding forces therebetween.

In one embodiment, the lifting action of the actuators serves to loosen target cells that are ready for harvest. After the target cells are loosened from adjacent cells, the loosened target cells can be collected by a known technique, such as scraping, tweezers, filtering, and the like. As discussed above, the target cells may be mature cultured cells, undesirable cells, or any cell that is desired to be harvested. Generally, a cell that has been loosened by an actuator is referred to as a "target cell." The lifting action of the actuators assists harvesting of target cells by loosening bonds and, in some cases, raising target cells higher than other cells for ease in grasping with an instrument, such as tweezers.

In another embodiment, some of the actuators may have feeder cells located thereon while other actuators have adhesive cells (i.e., target cells) that culture while adhering to the feeder cells. When the adhesive cells (i.e., target cells) are mature, the actuators on which the adhesive cells (i.e., target cells) are located can be activated to loosen the adhesive cells for culture. A suspension fluid can be poured into culture container to suspend the loosened adhesive cells (i.e., target cells). The suspension fluid can be a culture medium such as, but not limited to saline, bovine serum, nutrients, and the like. The suspension fluid raises the loosened adhesive cells (i.e., target cells) into suspension above the other cells in the culture. In one embodiment, raising the loosened adhesive cells (i.e., target cells) above the other cells allows for the loosened target cells to be more easily grasped by tweezers, filtered by a nylon mesh filter (e.g., manufactured by Miltenyi biotec of Bergisch Gladbach, Germany), and the like, for harvesting.

Figure 5A:
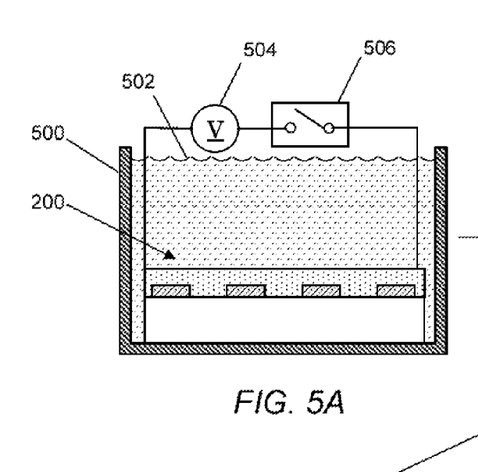
FIG. 5A through FIG. 5E illustrate side views of an illustrative embodiment of one embodiment of a cell culture vessel including a self-releasing, tissue cultivating device, through various stages of tissue culture and release.
Figure 5B:
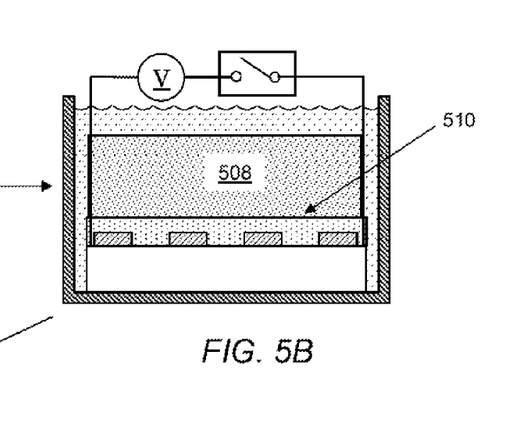

An example of a cell culture and peel is illustrated in FIG. 5A through FIG. 5B. A self-releasing, tissue cultivating platform 200 is placed in a bottom of a cell culture chamber 500. A cell culture solution 502 is introduced into the chamber, such that a supportive surface of the tissue cultivating platform 200 is exposed to the cell culture solution 502 (FIG. 5A). Cells and/or tissue is introduced into the chamber and a cell culture is grown over a period of time, through techniques well known to those familiar with cell cultivation or tissue engineering. The cell culture can form a layer, such as the tissue layer 508 illustrated along the supportive surface of the tissue cultivating platform 200 (FIG. 5B). Actuators of the tissue cultivating platform 200 are selectively coupled to an energy source 504 to induce actuation. A single switch is illustrated in schematic form to illustrate that energy can be selectively applied to one or more of the actuators according to the processes and techniques described herein.

Figure 5C:
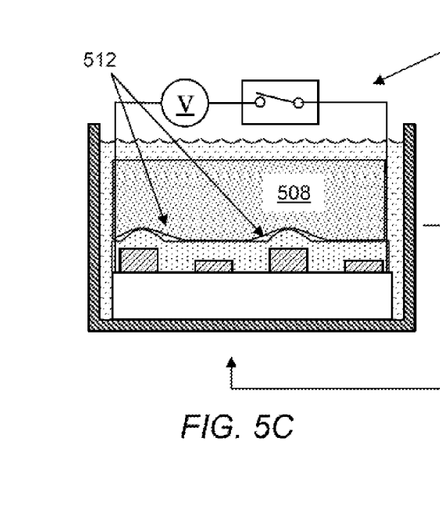
Figure 5D:
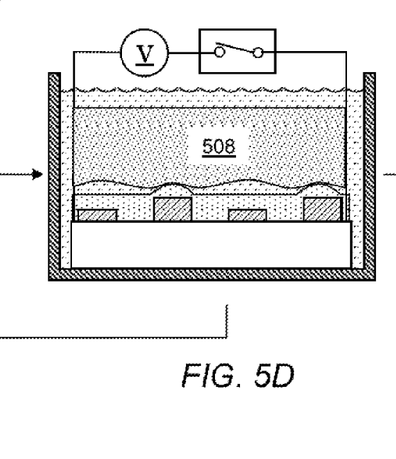
Figure 5E:
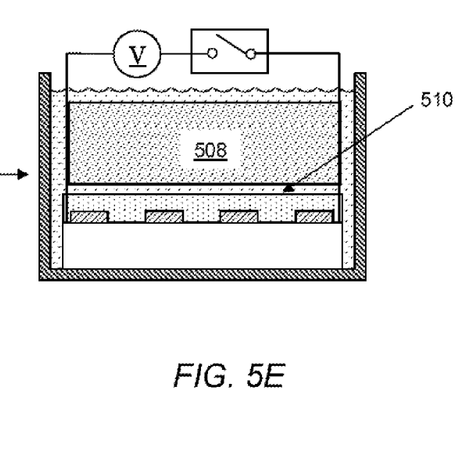

Referring next to FIG. 5C, a first subset of actuators is energized, expanding causing a localized deformation of the supportive surface, which results in a partial peeling 512 of the tissue 508 in the vicinity of the deformation. A second set of actuators is energized (FIG. 5D) in a similar manner, resulting in further peeling of the tissue 508. The process illustrated in FIG. 5C and FIG. 5D can be repeated in succession one or more times to loosen or otherwise free the tissue 508 from the supportive surface. The peel may be assisted or otherwise completed with mechanical means, such as tweezers, and the like.

The device can be used for various cell cultures with various shape of containers.

Culture method depends on the type of the cells to be cultured.

Figure 6:
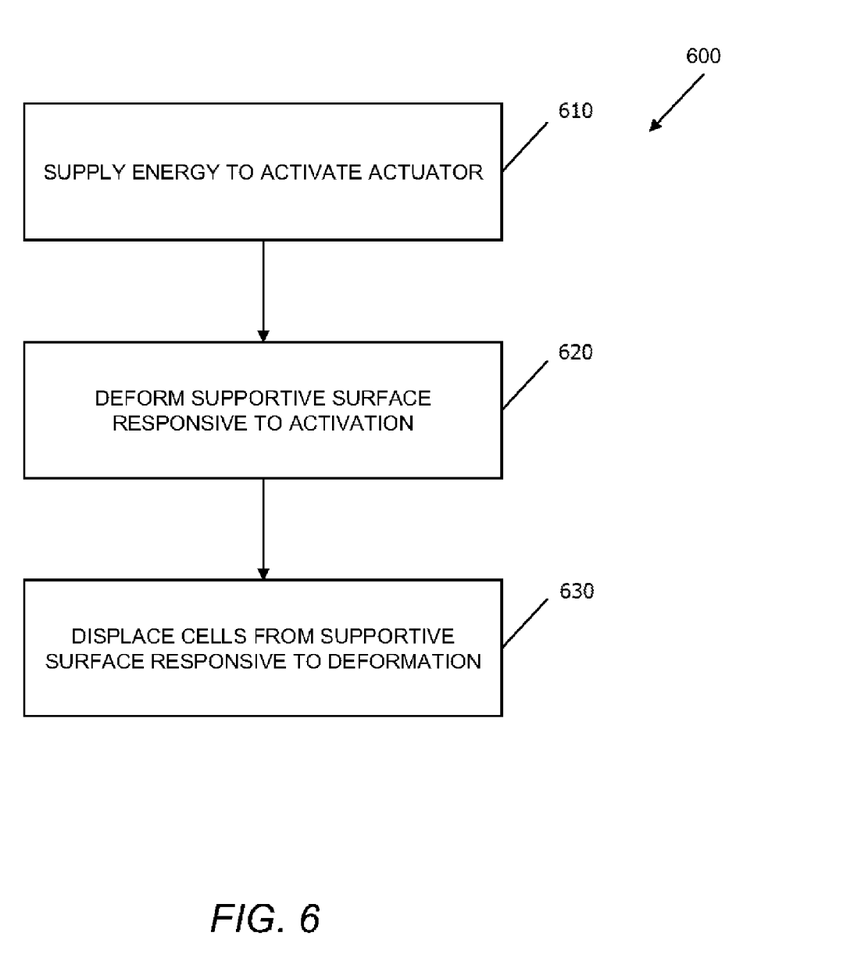
FIG. 6 illustrates a flow diagram of an illustrative embodiment of a process to facilitate harvesting of cultivated cells.

FIG. 6 illustrates a flow diagram of an illustrative embodiment of a process 600 to facilitate harvesting of cultivated cells. Energy is supplied at 610 to activate the at least one actuator positioned between a substrate surface and a supportive surface of a cell culture chamber configured to support one or more cells thereon. At least a portion of the supportive surface is deformed at 620 in responsive to activation of the at least one actuator. Such deformation is configured to at least partially displace one or more cells supported thereon at 630 relative to the supportive surface.

Figure 7:
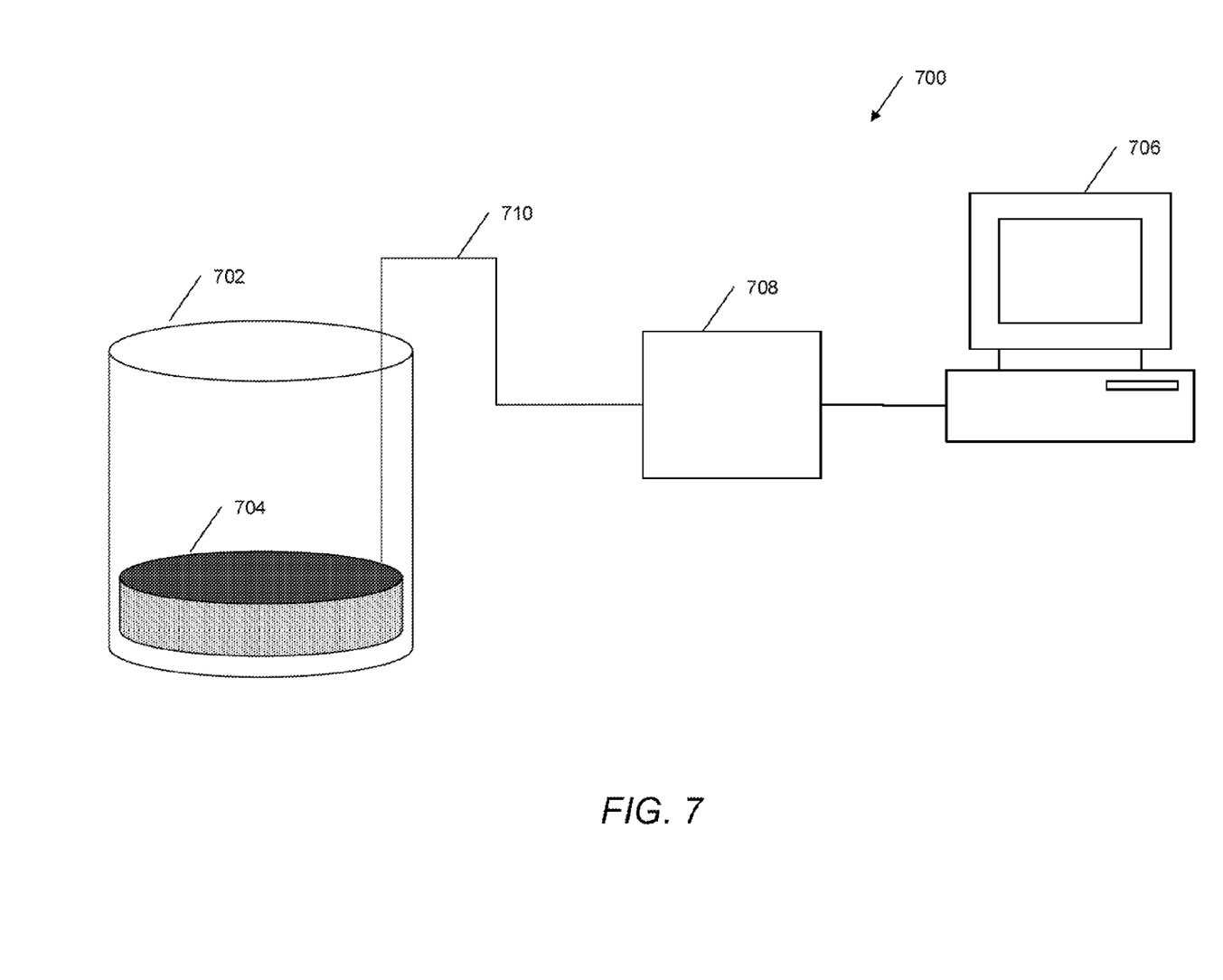
FIG. 7 illustrates a schematic diagram of another illustrative embodiment of a self-releasing, tissue cultivating device.

FIG. 7 illustrates a schematic diagram of another illustrative embodiment of a self-releasing, tissue cultivating system 700. The system includes a cell processing chamber 702, a cell-releasing substrate 704, a controller 706 adapted for controlling operation of the cell-releasing substrate 704, and a means for communication 708, 710 between the controller 706 and the cell-releasing substrate 704. The controller 706 controls activation of one or more actuators of the cell-releasing substrate 704 to promote peeling of at least a portion of cells cultured on a supportive surface of the cell-releasing substrate 704. The communication means 708, 710 conveys signals from the controller 706 to the cell-releasing substrate 704.

In some embodiments, the controller includes a microprocessor, such as a programmable processor of a general purpose computer. Alternatively or in addition, the controller can include a dedicated processor re-programmed for operation of the cell-releasing substrate 704. In some embodiments, the controller 706 can be an embedded controller modular with the cell-releasing substrate 704.

In some embodiments, the communication means includes at least one interconnecting lead 710. The lead can include an electrically conducting lead, an optical fiber lead, or a combination of electrically conducting and optical fiber leads. In some embodiments, such a lead 710 extends between the cell-releasing substrate 704 and the controller 706. Alternatively or in addition, the communication means includes a communications network 708. The communications network 708 can be one or more of a local area network and a wide area network, such as the Internet. The communications network 708 can conform to a standard network protocol, such as Ethernet and general purpose interface bus.

EQUIVALENTS

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third, and upper third, etc. As will also be understood by on skilled in the art all language such as "up to," "at least," "greater than," "less than," and the like include the number recited and refer to ranges, which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and not intended to be limiting, with the true scope and spirit being indicated by the following claims.

What is claimed is:

1. A cell cultivation platform comprising:
    a substrate having a surface;
    a plurality of actuators positioned relative to the surface of the substrate and configured to include at least two conformations, wherein a first subset of the plurality of actuators are in a normally contracted position and a second subset of the plurality of actuators are in a normally extended position;
    a deformable material layer at least partially covering the surface of the substrate and the plurality of actuators, wherein the deformable material layer is in direct contact with at least a portion of the surface of the substrate and at least a portion of each of the plurality of actuators, wherein the deformable material layer is a biocompatible supportive surface configured to deform in response to a change in conformation of the plurality of actuators, wherein the deformation displaces one or more cells of a cultured tissue sample relative to the biocompatible supportive surface, wherein the deformation that displaces the one or more cells results from an extension of the first subset of the plurality of actuators and a contraction of the second subset of the plurality of actuators; and
    a controller configured to control the plurality of actuators such that the first subset of the plurality of actuators extends in unison while the second subset of the plurality of actuators contracts in unison.

2. The cell cultivation platform of claim 1, wherein at least one actuator in the plurality of actuators is a piezoelectric actuator.

3. The cell cultivation platform of claim 1, wherein the plurality of actuators are piezoelectric actuators comprising Gallium orthophosphate ($GaPO_4$).

4. The cell cultivation platform of claim 1, wherein at least one actuator in the plurality of actuators has a diameter between about 100 nanometers (nm) and about 5 millimeters (mm).

5. The cell cultivation platform of claim 1, wherein the plurality of actuators are spaced apart to define an interval between actuators between about 10 micrometers (μm) and about 5 millimeters (mm).

6. The cell cultivation platform of claim 1, wherein the plurality of actuators are arranged on the surface of the substrate as an array.

7. The cell cultivation platform of claim 6, wherein the array comprises at least one row.

8. The cell cultivation platform of claim 6, wherein the array comprises a lattice.

9. The cell cultivation platform of claim 1, wherein the substrate comprises glass.

10. The cell cultivation platform of claim 9, wherein the substrate is contoured according to a portion of a cell processing chamber.

11. The cell cultivation platform of claim 1, wherein the deformable material layer is polyurethane.

12. The cell cultivation platform of claim 11, wherein the deformable material layer is formed as a coating covering at least a portion of the surface of the substrate and the plurality of actuators.

13. The cell cultivation platform of claim 12, wherein a thickness of the deformable material layer above the surface of the substrate is sufficient to cover the at least one actuator, while allowing substantial deformation of the biocompatible supportive surface in response to activation of the plurality of actuators.

14. The cell cultivation platform of claim 1, wherein the substrate has an interdigitation portion around at least a portion of an edge configured for interlocking engagement with a corresponding interdigitation portion of a container wall.

15. The cell cultivation platform of claim 14, wherein the container wall is fitted with the corresponding interdigitation portion.

16. The cell cultivation platform of claim 1, further comprising at least one electrical lead in electrical communication with the plurality of actuators.

17. The cell cultivation platform of claim 16, further comprising:
- an energy source in electrical communication with the plurality of actuators through the at least one electrical lead; and
- at least one switch coupled between the plurality of actuators and the energy source.

18. The cell cultivation platform of claim 17, wherein the controller is in communication with the at least one switch, and wherein the controller is configured to operate the at least one switch according to a peel protocol.

19. A cell culture chamber comprising the cell cultivation platform according to claim 1.

20. A cell cultivation platform comprising:
- means for supporting cultured cells along at least a portion of a supportive surface relative to a cell culture chamber, wherein the supportive surface is in direct contact with a substrate and a plurality of actuators, wherein a first subset of the plurality of actuators are in a normally contracted position and a second subset of the plurality of actuators are in a normally extended position;
- means for supplying energy to activate the plurality of actuators positioned between the substrate and the supportive surface;
- wherein, responsive to activation, the plurality of actuators are configured to deform at least a portion of the supportive surface, wherein the deformation displaces one or more cells of a cultured tissue sample relative to the supportive surface, and wherein the deformation that displaces the one or more cells results from an extension of the first subset of the plurality of actuators and a contraction of the second subset of the plurality of actuators; and
- means for controlling the plurality of actuators such that the first subset of the plurality of actuators extends in unison while the second subset of the plurality of actuators contracts in unison.

* * * * *